United States Patent
Oda et al.

(10) Patent No.: US 8,423,379 B2
(45) Date of Patent: Apr. 16, 2013

(54) MEDICAL-INFORMATION MANAGEMENT NETWORK SYSTEM

(75) Inventors: Yasuharu Oda, Hino (JP); Kazunori Imai, Chofu (JP)

(73) Assignee: Olympus Medical Systems Corp., Tokyo (JP)

( * ) Notice: Subject to any disclaimer, the term of this patent is extended or adjusted under 35 U.S.C. 154(b) by 783 days.

(21) Appl. No.: 12/581,380

(22) Filed: Oct. 19, 2009

(65) Prior Publication Data

US 2010/0041950 A1 Feb. 18, 2010

Related U.S. Application Data (63) Continuation of application No. PCT/JP2008/057604, filed on Apr. 18, 2008.

(30) Foreign Application Priority Data

Apr. 26, 2007 (JP) ................................. 2007-117586

(51) Int. Cl.
*G06Q 10/00* (2012.01)
(52) U.S. Cl.
USPC ................................... 705/2; 705/3; 600/300
(58) Field of Classification Search .................... 705/2, 3
See application file for complete search history.

(56) References Cited

U.S. PATENT DOCUMENTS

| 7,660,798 | B1 * | 2/2010 | Ludwig et al. ................... 726/11 |
| 2004/0073455 | A1 * | 4/2004 | McConnochie et al. .......... 705/2 |
| 2006/0014562 | A1 * | 1/2006 | Syrtsov et al. ............. 455/556.2 |
| 2006/0161960 | A1 * | 7/2006 | Benoit .......................... 725/105 |
| 2006/0165056 | A1 | 7/2006 | Komaki |
| 2007/0287891 | A1 * | 12/2007 | Horn ............................. 600/300 |

FOREIGN PATENT DOCUMENTS

| CN | 1689310 A | 10/2005 |
| JP | 2004-313242 | 11/2004 |
| JP | 2006-20971 | 1/2006 |
| JP | 2006-061627 | 3/2006 |

\* cited by examiner

*Primary Examiner* — Lena Najarian
(74) *Attorney, Agent, or Firm* — Scully, Scott, Murphy & Presser, P.C.

(57) ABSTRACT

A medical-information management network system includes a medical-information management server to which a server-identification information is individually given. The medical-information management server is configured to, for example, manage patient information, examination information, and a diagnosis result. The medical-information management server includes a receiving device that stores an in-vivo image, which is captured by a body-insertable apparatus inserted into a subject, and information received from the body-insertable apparatus, and an image display device that is connected with the medical-information management server via a network and obtains the in-vivo image and the information received from the body-insertable apparatus that are stored in the receiving device.

13 Claims, 12 Drawing Sheets

MEDICAL-INFORMATION MANAGEMENT NETWORK SYSTEM

CROSS-REFERENCE TO RELATED APPLICATIONS

This application is a continuation of PCT international application Ser. No. PCT/JP2008/057604 filed on Apr. 18, 2008 which designates the United States, incorporated herein by reference, and which claims the benefit of priority from Japanese Patent Application No. 2007-117586, filed on Apr. 26, 2007, incorporated herein by reference.

BACKGROUND OF THE INVENTION

1. Field of the Invention

The present invention relates to a medical-information management network system.

2. Description of the Related Art

In recent years, capsule endoscopes that have imaging and radio-communication functions have been developed in the field of endoscope. A capsule endoscope system has been proposed that uses such a capsule endoscope for capturing images of the inside of organs of a subject, sequentially receives the captured images with a receiving device, and sequentially displays the internal images of the subject that are received by the receiving device on an image display device, such as a workstation, so that the inside of the subject can be observed (examined).

Figure 11:
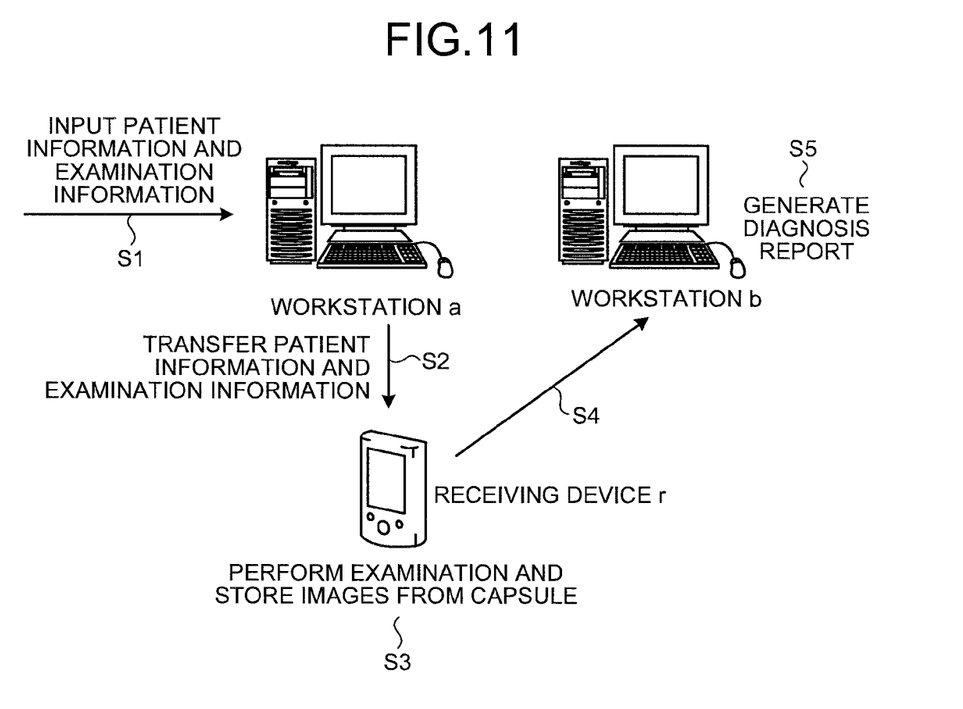
FIG. 11 is a schematic diagram showing an exemplary configuration of a conventional stand-alone apparatus.

In the capsule endoscope system, as shown in FIG. 11, patient information and examination information are manually input into a workstation a as the image display device at step S1 and then are transferred to a receiving device r at step S2. The receiving device r is detached from the workstation a and attached to a body surface of the subject. Then, the receiving device r stores as a maximum the number of images taken over an eight-hour period (about 60000 images) that are transmitted from a capsule endoscope that has been swallowed (step S3). After the capturing of images by the capsule endoscope, the receiving device r is detached from the subject and then connected to the workstation again (step S4). When a plurality of workstations exists, the receiving device r is connectable to any of the workstations. When the receiving device r is connected to, for example, a workstation b, the workstation b receives the large amount of images that have been stored in the receiving device r and performs an image observation and a diagnosis report generation.

The image display device, such as the workstation a or b, is conventionally operated as a stand-alone apparatus and does not have a function for managing the patient information (e.g., see Japanese Patent Application Laid-open No. 2006-61627). Therefore, for each diagnosis using a capsule endoscope, the patient information and the examination information are required to be input manually, for example, by operating a keyboard of the workstation, so that those information are transferred to the receiving device. This is troublesome.

If a medical-information management network system that includes a medical-information management server for managing diagnosis results or the like, to which image display devices are connected via a network, is constructed, the image display devices can utilize the patient information and the examination information input into and managed by the medical-information management server. This improves the usability.

SUMMARY OF THE INVENTION

A medical-information management network system according to an aspect of the present invention includes a medical-information management server to which a server-identification information is individually given, the medical-information management server configured to manage patient information, examination information, and a diagnosis result; a receiving device that stores an in-vivo image, which is captured by a body-insertable apparatus inserted into a subject, and information received from the body-insertable apparatus; and an image display device that is connected with the medical-information management server via a network and obtains the in-vivo image and the information received from the body-insertable apparatus that are stored in the receiving device.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 12:
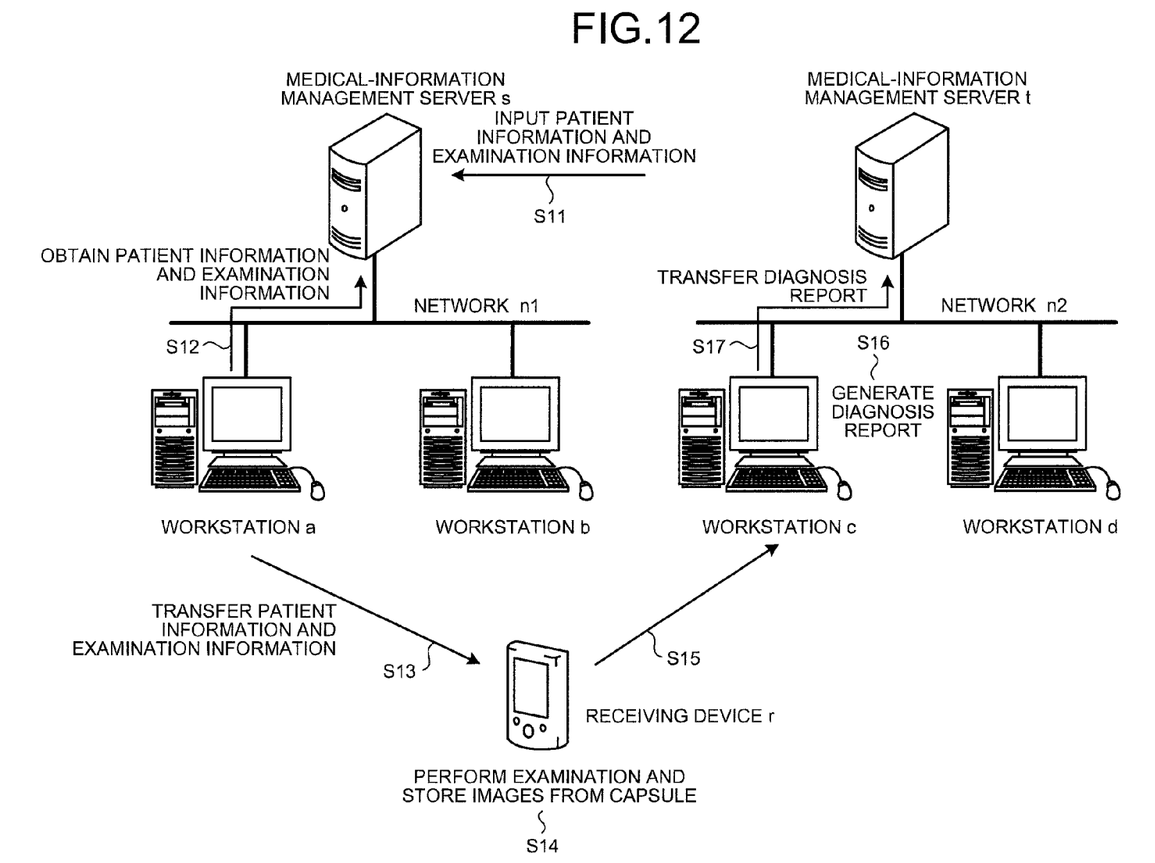
FIG. 12 is a schematic diagram showing an exemplary configuration of a conventional medical-information management network system.

FIG. 12 shows a hypothetical medical-information management network system. In FIG. 12, two medical-information management servers s and t are connected to different networks n1 and n2, respectively. Workstations a and b are connected to the network n1 of the medical-information management server s while workstations c and d are connected to the network n2 of the medical-information management server t. The medical-information management servers s and t are located at, for example, the department of internal medicine and the department of external medicine in the same hospital, respectively. The medical-information management servers s and t manage patient information, examination information, and the like that are independently input. The examination information includes examination-identification information (examination ID) that differs for each examination.

Under such a system environment, before performing an endoscope examination, the patient information and the examination information and the like are first input to the medical-information management server s through client terminals or the like (Step S11). Before performing the endoscope examination, for example, the workstation a searches the medical-information management server s to obtain desired patient information and examination information (including the examination ID) (Step S12), and transfers the obtained patient information and examination information to the receiving device r (Step S13). The receiving device r is detached from the workstation a and attached to the body surface of the subject. Then, the receiving device stores therein as a maximum the number of images taken over an eight-hour period (about 60000 images) that are transmitted from the swallowed capsule endoscope (Step S14). After capturing of images by the capsule endoscope, the receiving device r is detached from the subject and connected to the workstation again.

The receiving device r can be connected to any of workstations when there is a plurality of workstations. When the receiving device r is connected to the workstation a or the workstation b, there is no problem. When the receiving device r is, for example, connected to the workstation c (Step S15), the large amount of images stored in the receiving device r is transferred to the workstation c. Then, the workstation c performs observation of images and generates a diagnosis report (Step S16). When the workstation c transfers the diagnosis report to the medical-information management server t (Step S17), the medical-information management server t uploads and registers the transferred diagnosis report. In this case, the patient information and the examination information of the transferred diagnosis report are not registered in the medical-information management server t. The examination ID of another patient, which the medical-information management server t has independently appended, may be overwritten, and patients may be mixed up.

Exemplary embodiments of a medical-information management network system in accordance with the present invention are described in detail with reference to accompanying drawings. Not limited to each of the embodiments, the present invention can be modified in various ways without departing from the spirit of the present invention; therefore, each of those embodiments does not limit the scope of the invention.

First Embodiment

Figure 1:
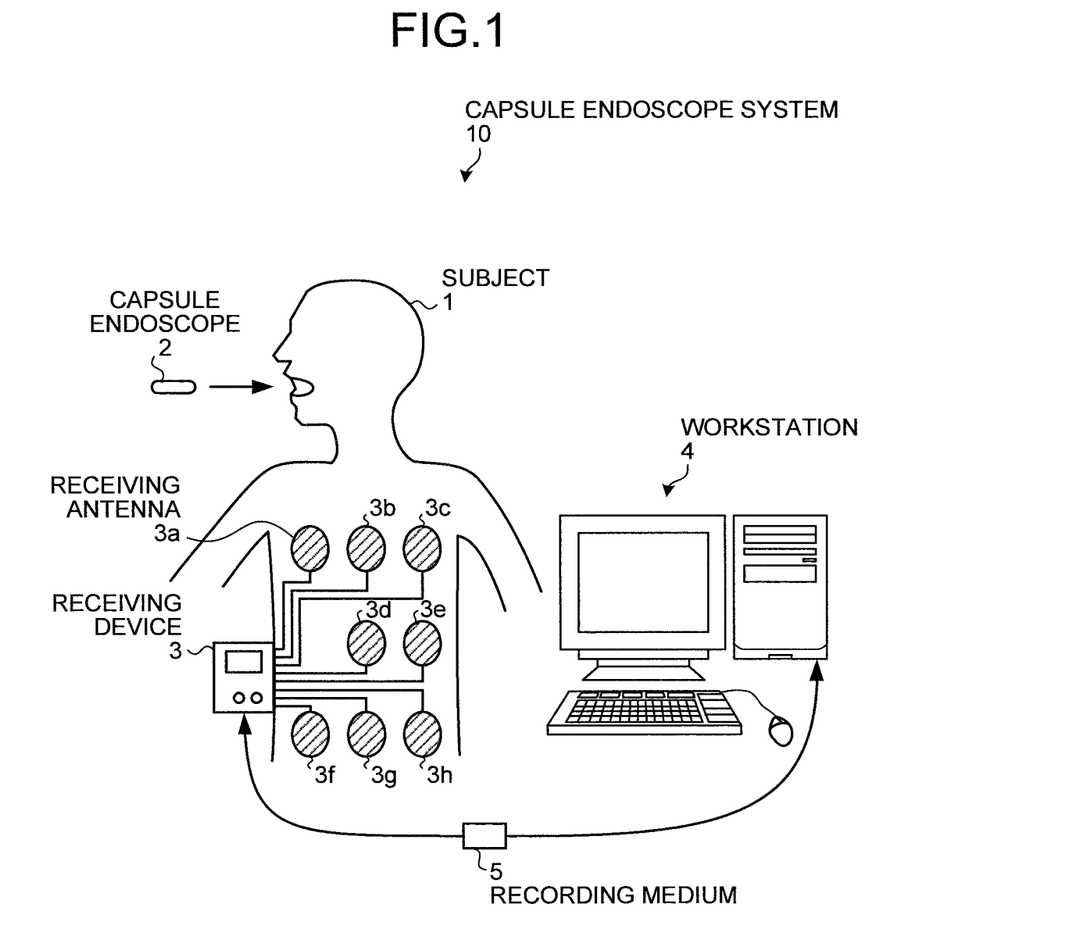
FIG. 1 is a schematic diagram showing an exemplary capsule endoscope system in a first embodiment of the present invention.

Prior to the description of the medical-information management network system according to a first embodiment, an outline of a capsule endoscope system is described. FIG. 1 is a schematic diagram showing an exemplary capsule endoscope system in a first embodiment of the present invention. As shown in FIG. 1, a capsule-endoscope system 10 includes a capsule endoscope 2 that is a body-insertable apparatus and captures in-vivo images of a subject 1, such as a patient, a receiving device 3 that receives the in-vivo images of the subject 1 from the capsule endoscope 2 and stores therein these images, a workstation 4 that obtains and displays in-vivo image information on the subject 1, which is received and stored by the receiving device 3, and performs other predetermined processes on the information, and a portable recording medium 5 for transferring data between the receiving device 3 and the workstation 4.

The capsule endoscope 2 captures in-vivo images of the subject 1. The capsule endoscope 2 has imaging and radio-communication functions in its capsule-shaped casing that is insertable into organs of the subject 1. Specifically, the capsule endoscope 2 is swallowed from the mouth of the subject 1. While moving through organs of the subject 1 due to peristalsis or the like of the organs, the capsule endoscope 2 sequentially captures in-vivo images of the subject 1 at predetermined intervals (e.g., 0.5-second intervals). The capsule endoscope 2 then sequentially and wirelessly transmits in-vivo information including in-vivo images of the subject 1 to the external receiving device 3. The capsule endoscope 2 has a capsule ID that identifies each individual capsule endoscope 2. The capsule ID is appended to image signals that include captured image data. Such a capsule endoscope 2 sequentially and wirelessly transmits the image data, such as in-vivo images, together with its capsule ID to the external receiving device 3.

The receiving device 3 wirelessly receives and stores therein the in-vivo images of the subject 1 that are captured by the capsule endoscope 2. In detail, the receiving device 3 includes a plurality of receiving antennas 3a to 3h and is attached to (carried by) the subject 1, who has the capsule endoscope 2 inserted into organs. The receiving device 3 sequentially receives the image signals that are wirelessly transmitted from the capsule endoscope 2 via the receiving antennas 3a to 3h and obtains the image data and capsule ID included in the image signal. Furthermore, the receiving device 3 includes the recording medium 5 and stores in the recording medium 5 the in-vivo images of the subject 1 and the capsule ID that are received from the capsule endoscope 2.

The workstation 4 obtains various types of data, such as in-vivo images of the subject 1, from the recording medium 5 and has a function as an image display device for displaying those obtained various types of data on a display. The workstation 4 displays the in-vivo images of the subject 1 obtained from the recording medium 5. The in-vivo images of the subject 1 displayed by the workstation 4 are observed (examined) by users, such as doctors and nurses, and thus the subject 1 is diagnosed. Furthermore, the workstation 4 has a report generating function for generating a diagnosis report that shows a diagnosis result of the subject 1 and other information. User comments are described on the diagnosis report. The workstation 4 displays the generated diagnosis report on the display.

The recording medium 5 is a portable recording medium and is used for transferring data between the receiving device 3 and the workstation 4 described above. In detail, the recording medium 5 can be attached to and detached from the receiving device 3 or the workstation 4 and, when inserted into the receiving device 3 or the workstation 4, the recording medium 5 can output data or store data. When inserted into the receiving device 3, the recording medium 5 stores therein in-vivo images of the subject 1 and the like that are received by the receiving device 3 from the capsule endoscope 2. When inserted into the workstation 4, the recording medium 5 outputs the stored data, such as in-vivo images of the subject 1, to the workstation 4. In the present embodiment, the portable recording medium 5 is used for transferring data between the receiving device 3 and the workstation 4; therefore, the recording medium 5 is a component of the receiving device 3. Alternatively, the receiving device 3 may be directly connected to the workstation 4 so that data can be transferred.

The various types of data stored in the recording medium 5 are, for example, an in-vivo image group of the subject 1, time information (e.g., capture times and reception times) of each in-vivo image in the in-vivo image group, the capsule ID of the capsule endoscope 2 that has captured the in-vivo image group of the subject 1, patient information on the subject 1, and examination information on the subject 1. The patient information on the subject 1 is information for identifying the subject 1, e.g., patient name, patient ID, birth date, sex, and age. The examination information on the subject 1 is information for identifying a capsule endoscope examination (an examination in which the capsule endoscope 2 is inserted into organs in order to observe inside of the organs) that is performed on the subject 1, e.g., examination ID and examination date, which differ for each examination.

Figure 2:
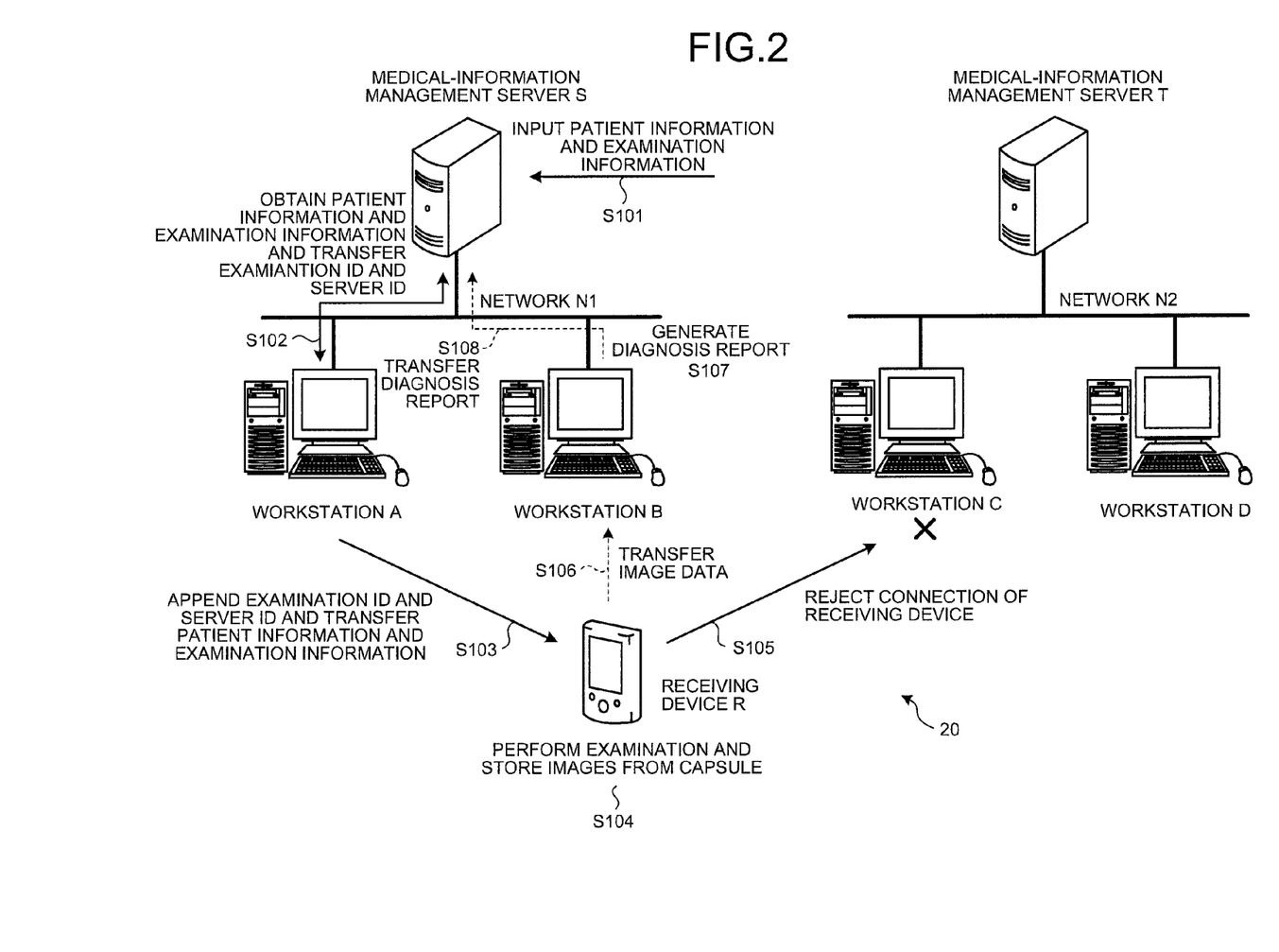
FIG. 2 is a schematic diagram showing an exemplary configuration of a medical-information management network system in accordance with the first embodiment.

A medical-information management network system in accordance with the first embodiment that includes the receiving device 3 (including the recording medium 5) and the workstation 4 is described below. FIG. 2 is a schematic diagram showing an exemplary configuration of a medical-information management network system in accordance with the first embodiment. The medical-information management network system 20 includes a plurality of medical-information management servers S and T, a receiving device S, a plurality of workstations A to D, and networks N1 and N2. The medical-information management server S is connected with the workstations A and B on the one network N1. The medical-information management server T is connected with the workstations C and D on the other network N2.

The medical-information management server S manages the patient information and the examination information that are input through the client terminals or the like as described above and further manages the diagnosis result transferred from the workstations A and B. The medical-information management server T manages, independently from the medical-information management server S, the patient information and the examination information that are input through the client terminals or the like as described above and further manages, independently from the medical-information management server S, the diagnosis result transferred from the workstations C and D. The networks N1 and N2 are constructed with the Internet, an intranet, a wired LAN, a wireless LAN, or the like. The workstations A to D correspond to the workstations 4 described above. The receiving device R corresponds to the receiving device 3 described above and includes the recording medium 5.

Figure 3:
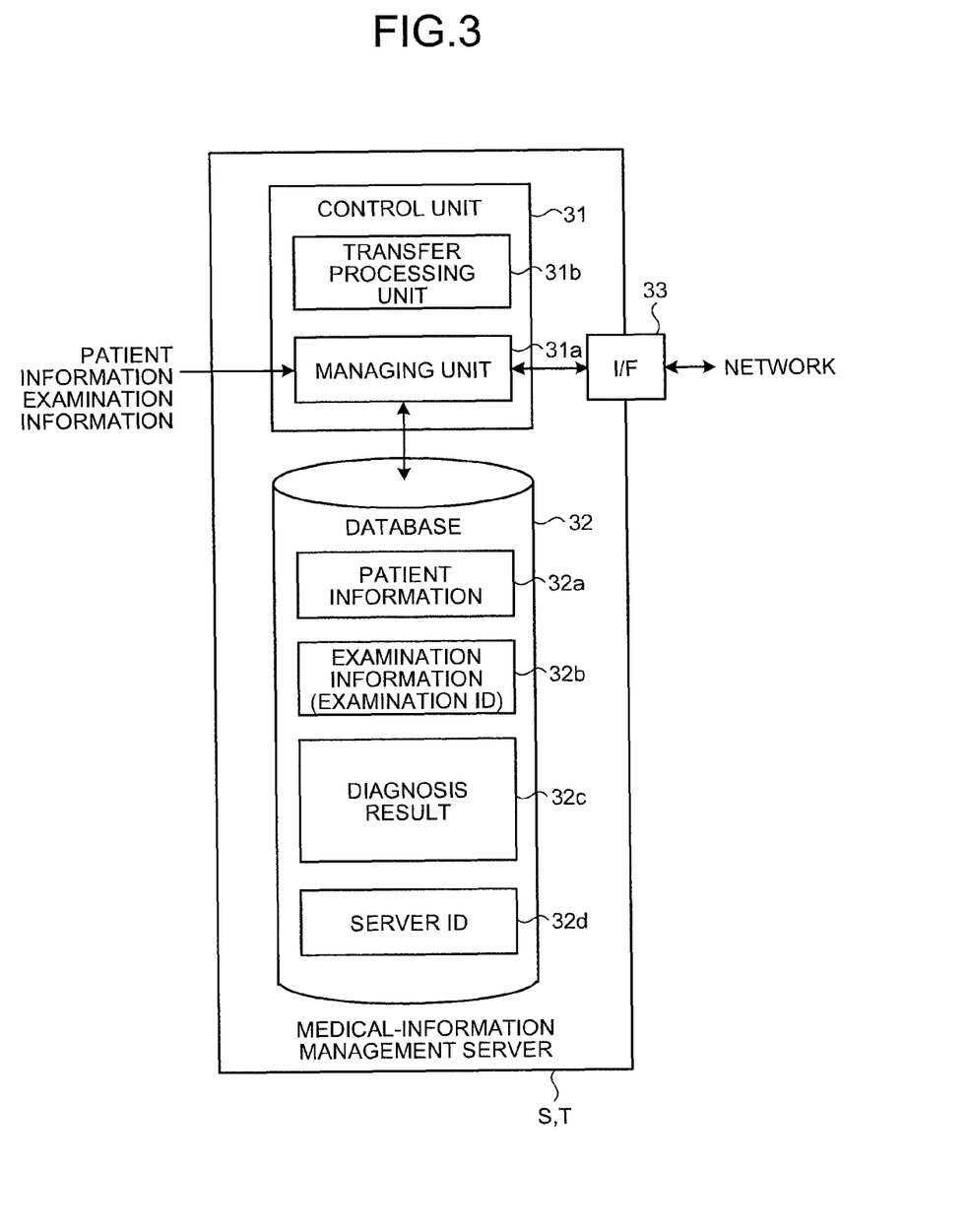
FIG. 3 is a block diagram showing an exemplary configuration of a medical-information management server.

An exemplary configuration of the medical-information management servers S and T is described with reference to FIG. 3. FIG. 3 is a block diagram showing an exemplary configuration of the medical-information management servers S and T. The medical-information management servers S and T include a control unit 31, a database 32 and an interface (I/F) 33. The interface 33 enables connections between the management servers S and T and the networks N1 and N2. The control unit 31 includes a managing unit 31a and a transfer processing unit 31b. The managing unit 31a performs a process to store the patient information and the examination information that are input from external client terminals or the like in a patient information storage area 32a and an examination information storage area 32b in the database 32, respectively. An examination ID, which is an examination-identification information and differs for each examination, is appended to the examination information. The appending of the examination ID is independently performed by each of the medical information management servers S and T. The managing unit 31a performs a process to store the diagnosis results transferred from the workstations A to D on the networks N1 and N2 in a diagnosis-result storage area 32c in the database 32. The diagnosis results are stored in association with the patient information, the examination information, and the like.

The medical-information management servers S and T in accordance with the embodiment are given server IDs, which are server-identification information that differ for each of the medical-information management servers S and T. Under the control of the managing unit 31a, the medical-information management servers S and T store the given server IDs in a server-ID storage area 32d in the database 32. The server ID may be generated using a combination of hardware or network-identification information (e.g., IP address and MAC address). Alternatively, the server IDs may be manually given and managed such that a redundant provision of a server ID for medical-information management servers is avoided.

When there is a request from the workstation to transfer the patient information and the examination, the transfer processing unit 31b in the control unit 31 refers to the database 32 before transferring the patient information and the examination information to the workstation performing the search. Then, the transfer processing unit 31b performs a process to append the examination ID and its server ID to the patient information and the examination information and then performs a process to transfer the patient information and the examination information.

Figure 4:
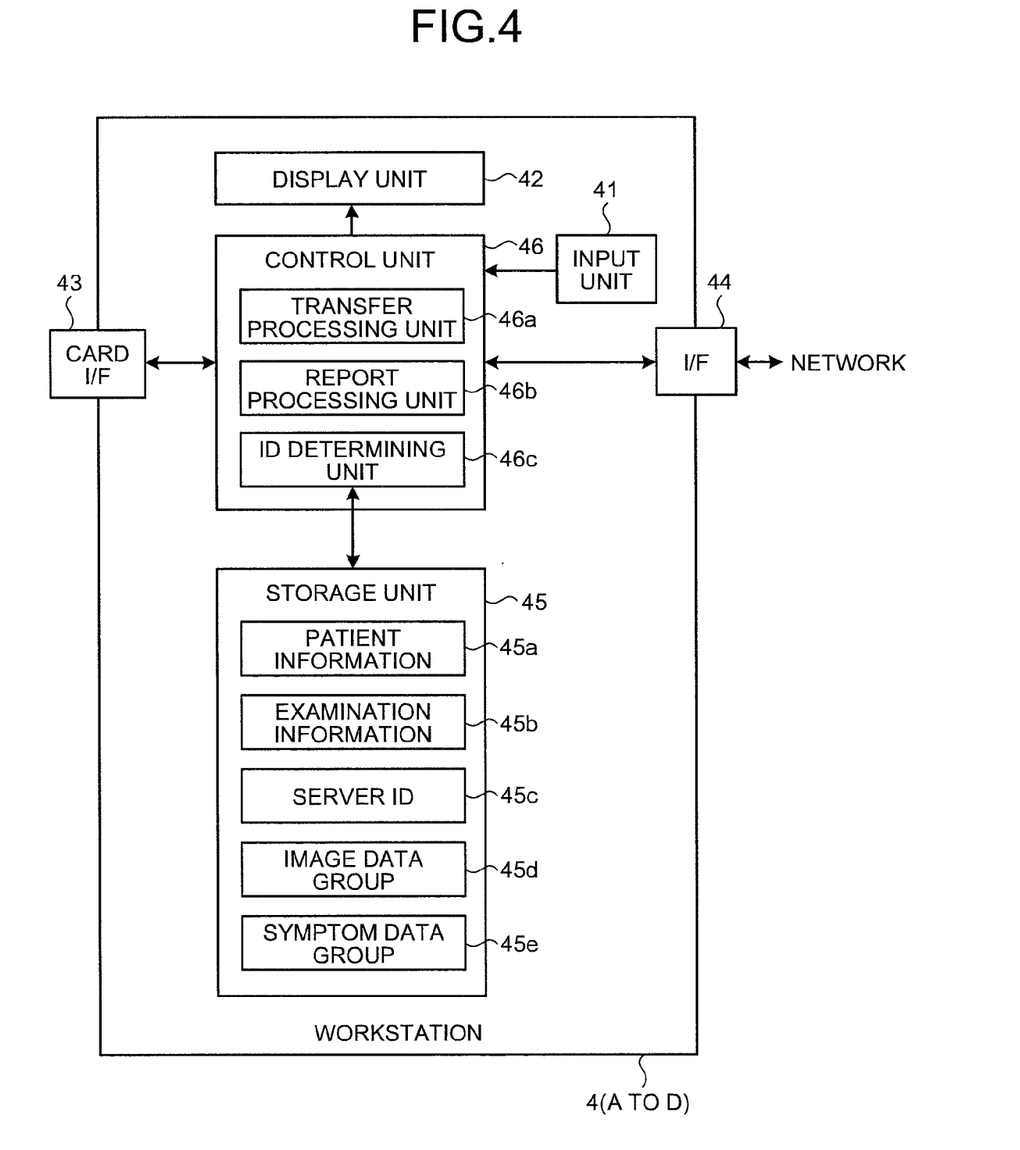
FIG. 4 is a block diagram showing an exemplary configuration of a workstation.

Subsequently, a configuration of the workstation 4 (A to D) is described. FIG. 4 is a block diagram showing an exemplary configuration of the workstation 4 (A to D). The workstation 4 includes an input unit 41 that inputs the various types of information, a display unit 42 that displays in-vivo images of the subject 1, and a card interface (I/F) 43 into which the recording medium 5 is inserted. Furthermore, the workstation 4 includes an interface (I/F) 44 that allows the workstation 4 to communicate information with the medical-information management server S or T on the network N1 or N2, a storage unit 45 that stores various types of data such as in-vivo images of the subject 1, and a control unit 46 that controls the components of the workstation 4.

The input unit 41 can be constructed with a use of input devices such as a keyboard, a mouse, or the like. The input unit 41 inputs various types of information to the control unit 46 based on input operations from users. The display unit 42 can be constructed with a use of various types of displays such as a liquid crystal display or the like. The display unit 42 displays various types of information that are to be displayed corresponding to instructions from the control unit 46. For example, the display unit 42 displays in-vivo images of the subject 1 that are captured by the capsule endoscope 2, diagnosis reports on the subject 1, or the like. The recording medium 5 is inserted into the card I/F 43 in a manner such that the recording medium 5 can be detached therefrom. Then, the card I/F 43 enables data to be input or output between the inserted recording medium 5 and the control unit 46. The interface 44 is connected, for communication, with the medical-information management server S or T on the network N1 or N2 so that information is communicated.

The storage unit 45 can be constructed with a use of various types of storage mediums, such as a RAM, EEPROM, flash memory, and hard disk, which can store data therein in a rewritable manner. The storage unit 45 stores various types of data that are to be stored based on instructions from the control unit 46. The storage unit 45 transfers data, in the various types of stored data, that is to be read based on instructions from the control unit 46 to the control unit 46. The storage unit 45 includes storage areas 45a to 45c that respectively store the patient information, the examination information, and the server ID transmitted from the medical-information management server S or T. Furthermore, the storage unit 45 includes a storage area 45d that stores the image data group transferred from the receiving device 3 (R) (the information medium 5) and a storage area 45e that stores an examination data group indicating symptoms of a plurality of subjects. An examination data on a subject included in the examination data group includes an in-vivo image group of the subject, patient information, examination information, time information of each in-vivo image, and diagnosis report information.

The control unit 46 controls the components (the input unit 41, the display unit 42, the card I/F 43, the interface 44, and the storage unit 45) of the workstation 4 and controls input and output of signals among these components. Furthermore, the control unit 46 reads the examination data of a desired subject from the examination data group based on instruction information that is input from the input unit 41. The control unit 46 then displays on the display unit 42 the in-vivo image group and the like of the subject included in the examination data being read. The control unit 46 in the first embodiment includes a transfer processing unit 46a, a report processing unit 46b, and an ID determining unit 46c. The transfer processing unit 46a refers to the storage unit 45 before transferring the patient information and the examination information to the receiving device 3 (R). Then, the transfer processing unit 46a performs a process to append the examination ID and the server ID thus searched to the patient information and the examination information and performs a process to transfer the patient information and the examination information.

The report processing unit 46b functions as a report generating unit that generates, based on the examination data of the subject selected from the examination data group, a diagnosis report on the subject as a diagnosis result. The report processing unit 46b generates a diagnosis report that indicates, for example, all or some images selected from the in-vivo image group of the subject 1, the capsule ID of the capsule endoscope that has captured the in-vivo image group of the subject 1, the patient information of the subject 1, the diagnosis result of the subject 1, and the like.

Furthermore, the ID determining unit 46c retains therein the server ID of the medical-information management server with which the workstation itself is currently connected. The ID determining unit 46c rejects a connection of the receiving device 3 (R) that stores a server ID different from the retained server ID. The ID determining unit 46c controls an authorization of an access of the receiving device 3, which has completed the examination, to the medical-information management server via the workstation.

Figure 5:
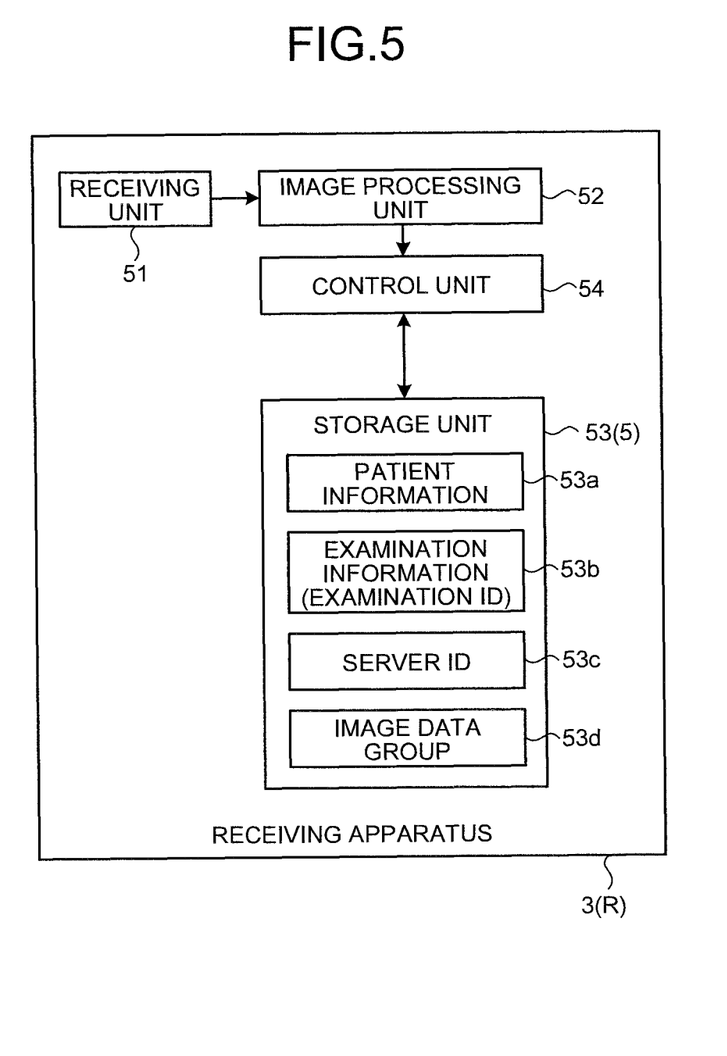
FIG. 5 is a block diagram showing an exemplary configuration of a receiving device.

Furthermore, a configuration of the receiving device 3 (R) (the information medium 5) is described. FIG. 5 is a block diagram showing an exemplary configuration of the receiving device 3 (R) (the information medium 5). The receiving device 3 includes a receiving unit 51 that receives images signals transmitted wirelessly from the capsule endoscope 2, an image processing unit 52 that generates in-vivo images of the subject 1 based on the image signals, a storage unit 53 into which the information medium 5 described above is inserted, and a control unit 54 that controls each of the components of the receiving device 3. The storage unit 53, which corresponds to the information medium 5, includes storage areas 53a, 53b, and 53c that store the patient information, the examination information (including the examination ID), and the server ID transmitted from the workstation before the examination. Furthermore, the storage unit 53 includes a storage area 53d that stores the image data group obtained, during the examination, from the capsule endoscope 2.

In such a system configuration, an exemplary operation control of the system is described with reference to FIG. 2. Before the endoscope examination, the patient information, the examination information, and the like are input from the client terminals or the like to the medical-information management server S (Step S101). The same applies to the medical-information management server T. Furthermore, before the endoscope examination, the workstation A accesses to the medical-information management server S on the network N1, to which the workstation A is connected, and obtains the desired patient information and the examination information transferred from the medical-information management server S (Step S102). The transfer processing unit 31b in the medical-information management server S appends the examination ID and its server ID to the patient information and the examination information and transfers the patient information and the examination information at Step S102.

The workstation A subjected to the transfer process then transfers the patient information and the examination information obtained through the transfer process to the receiving device R (Step S103). The transfer processing unit 46a in the workstation A appends the examination ID and the server ID, which have been transferred and stored, to the patient information and the examination information at Step S103 and transfers the patient information and the examination information. Accordingly, the patient information, the examination information (including the examination ID), and the server ID are stored in the storage unit 53 of the receiving device R. The receiving device R (the information medium 5) is detached from the workstation A and attached to the body surface of the subject 1. Then, the receiving device R stores therein as a maximum the number of images taken over an eight-hour period (about 60000 images) that are transmitted from the swallowed capsule endoscope 2 (Step S104). After the examination using the capsule endoscope 2, the receiving device R is detached from the subject 1 and connected to the workstation again.

It is assumed that the receiving device R (the information medium 5) is connected to the workstation C. In this case, the ID determining unit 46c in the workstation C retains therein the server ID of the medical-information management server T, with which the workstation C is connected. The server ID transferred to and stored in the connected receiving device R (the information medium 5) is for the medical-information management server S and therefore does not match the retained server ID. Therefore, the ID determining unit 46c rejects the transfer of the image data to the workstation C with the connection of the receiving device R, as indicated by x mark (Step S105). The same applies to a case where the receiving device R (the information medium 5) is connected to the workstation D. A warning to an effect that the server IDs do not match is displayed by the display unit 42 in the workstation C. The same applies to a case where the receiving device R (the information medium 5) is connected to the workstation D.

Next, it is assumed that the receiving device R (the information medium 5) is connected to the workstation B. In this case, the ID determining unit 46c in the workstation B retains therein the server ID of the medical-information management server S, with which the workstation B is connected. The server ID transferred to and stored in the connected receiving device R (the information medium 5) is also for the medical-information management server S and therefore matches the retained ID. Thus, the image data is transferred from the receiving device R (the information medium 5) to the workstation B (Step S106). In the workstation B, the report processing unit 46b generates a diagnosis report as a diagnosis result (Step S107) and transfers the diagnosis report to the medical-information management server S via the network N1 (Step S108). The medical-information management server S stores and manages the transferred diagnosis report, in association with the examination ID and the like stored therein. The same applies to a case where the receiving device R (the information medium 5) is connected to the workstation A.

Using the server ID as described above, the medical-information management server that has provided the patient information and the examination information can be always identified. The trouble of transferring a diagnosis result to a medical-information management server and storing therein, the server being different from the server that has provided the patient information and examination information, is reliably avoided at the time of transfer to the workstation. Thus, the corresponding diagnosis result is managed at the medical-information management server that has provided the patient information and the examination information.

Second Embodiment

Figure 6:
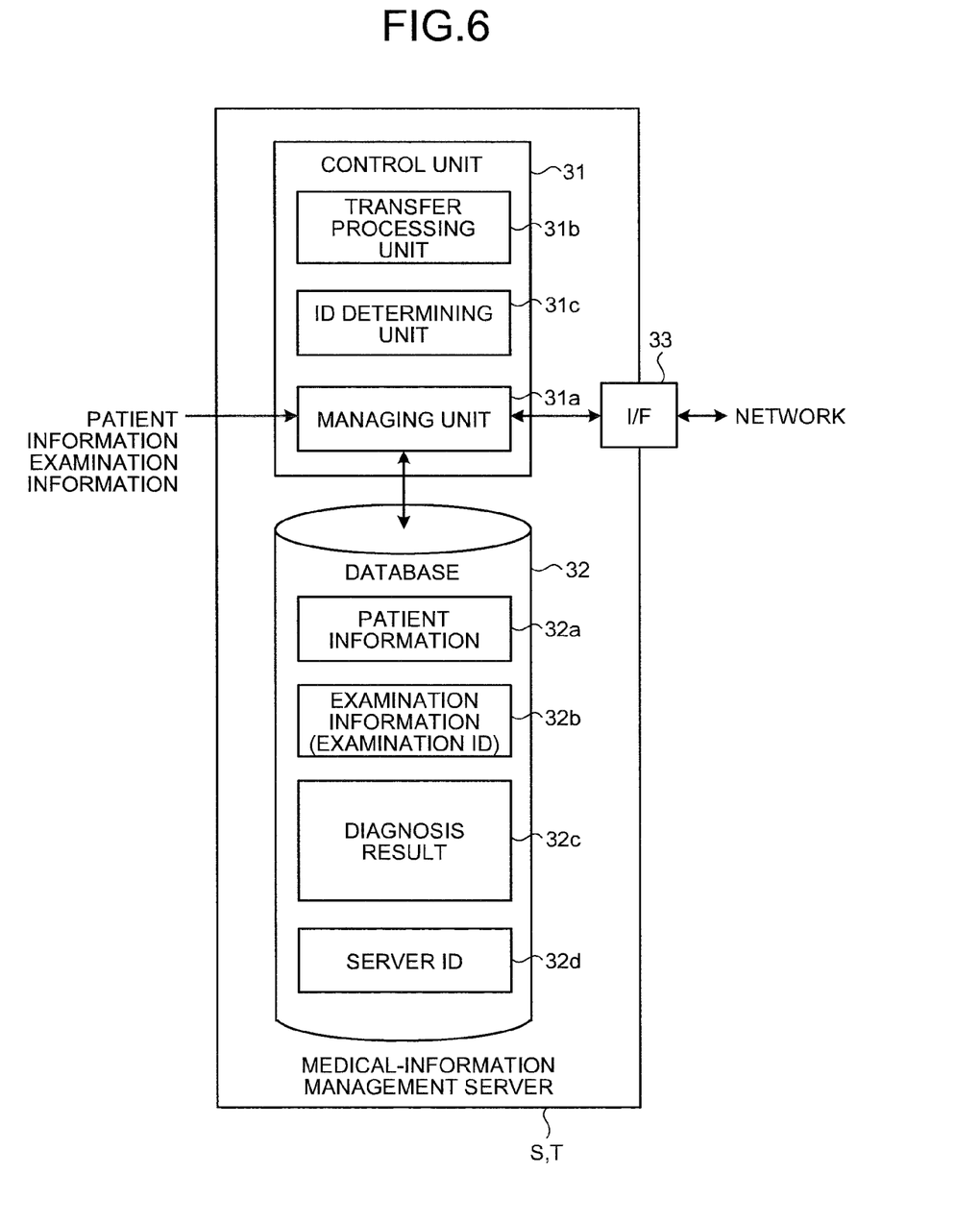
FIG. 6 is a block diagram showing an exemplary configuration of a medical-information management server in a second embodiment.
Figure 7:
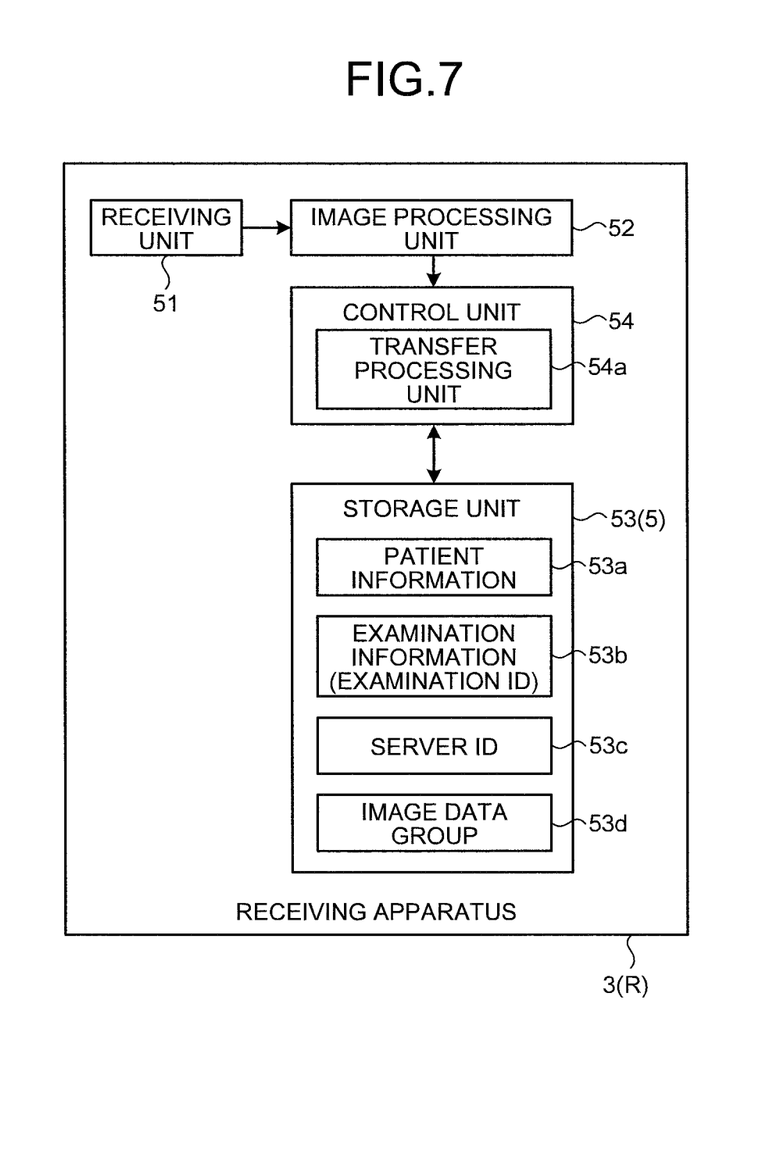
FIG. 7 is a block diagram showing an exemplary configuration of a receiving device.
Figure 8:
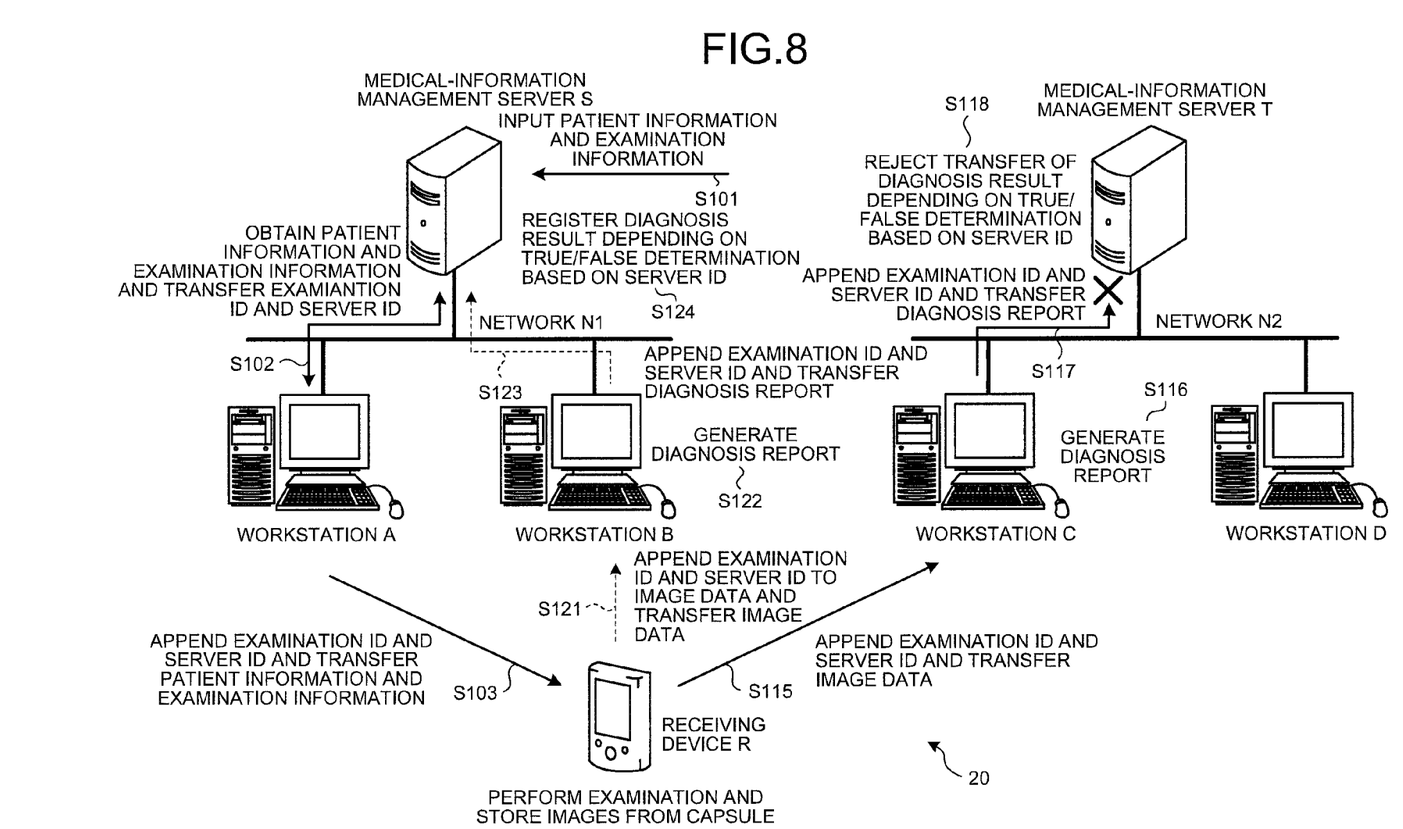
FIG. 8 is a schematic diagram showing an exemplary configuration of a medical-information management network system in accordance with the second embodiment.

A medical-information management network system in accordance with a second embodiment is described with reference to FIGS. 6 to 8. The components that are the same as or correspond to those in the first embodiment are denoted by the same numerals. FIG. 6 is a block diagram showing an exemplary configuration of medical-information management servers S and T in the second embodiment. FIG. 7 is a block diagram showing an exemplary configuration of the receiving device R. FIG. 8 is a schematic diagram showing an exemplary configuration of the medical-information management network system in accordance with the second embodiment.

In the second embodiment, instead of the workstation, the medical-information management servers S and T include the ID determining unit 31*c* in the control unit 31, and the receiving device R includes the transfer processing unit 54*a* in the control unit 54. The transfer processing unit 54*a* appends the examination ID and the server ID, which are transferred and stored beforehand, to the in-vivo image information when transferring the in-vivo image information to any of the workstations A to D that has completed the examination. Furthermore, the transfer processing unit 46*a* in the workstations A to D also has a function of appending the examination ID and the server ID, which are transferred and stored beforehand, to the diagnosis result when transferring the diagnosis result to the medical-information management servers S and T.

The ID determining unit 31*c* in the control unit 31 determines, when the diagnosis result is transferred, whether the server ID notified from the workstations A to D is correct. When the server ID is incorrect, the ID determining unit 31*c* gives out a notification that the server ID is incorrect and controls an authorization of the access of the receiving device, which has completed the examination, to the medical-information management server via the workstation, such that the reception (upload) of the diagnosis result from the workstation is rejected.

In such a system configuration, an exemplary operation control of the system is described with reference to FIG. 8. This example is similar to that in FIG. 2. The processes up to Step S104 are the same as those in FIG. 2.

It is assumed that the receiving device R (the information medium 5) is connected to the workstation C after the examination is finished. In this case, the transfer processing unit 54*a* in the receiving device R appends the examination ID and the server ID, which are transferred and stored beforehand, to the in-vivo image information and transfers the in-vivo image information to the workstation C (Step S115). In the workstation C, the report processing unit 46*b* generates a diagnosis report as a diagnosis result (Step S116) and transfers the diagnosis report to the medical-information management server T via the network N2 (Step S117). The ID determining unit 31C in the medical-information management server C determines whether the server ID appended to the transferred diagnosis report is a correct one matching the server ID thereof. In this case, the server ID appended and transferred is for the medical-information management server S and does not match the server ID thereof. Therefore, the ID determining unit 31C rejects the transfer (upload) of the diagnosis result to the medical-information management server T from the workstation C, as indicated by x mark (Step S118). In this case, a warning to an effect that the server IDs do not match is displayed by the display unit 42 in the workstation C. The same applies to a case where the receiving device R (the information medium 5) is connected to the workstation D.

Next, it is assumed that the receiving device R (the information medium 5) is connected to the workstation B. In this case, the transfer processing unit 54*a* in the receiving device R appends the examination ID and the server ID, which are transferred and stored beforehand, to the in-vivo image information and transfers the in-vivo image information to the workstation B (Step S121). In the workstation B, the report processing unit 46*b* generates a diagnosis report as a diagnosis result (Step S122) and transfers the diagnosis report to the medical-information management server S via the network N1 (Step S123). The ID determining unit 31C in the medical-information management server B determines whether the server ID appended to the transferred diagnosis report is a correct one matching the server ID thereof. In this case, the server ID appended and transferred is for the medical-information management server S and therefore matches the server ID thereof. Thus, the medical-information management server S stores and manages the transferred diagnosis report in association with the examination ID or the like stored therein (Step S124). The same applies a case where the receiving device R (the information medium 5) is connected to the workstation A.

Using the server ID as described above, the medical-information management server that has provided the patient information and the examination information can be always identified. The trouble of transferring a diagnosis result to a medical-information management server and storing therein, the server being different from the server that has provided the patient information and examination information, is reliably avoided at the time of upload to the medical-information management server. In particular, the system is user-friendly because connecting the receiving device to any of the workstations and observing the image data stored in the receiving device are possible as are conventionally done.

Third Embodiment

Figure 9:
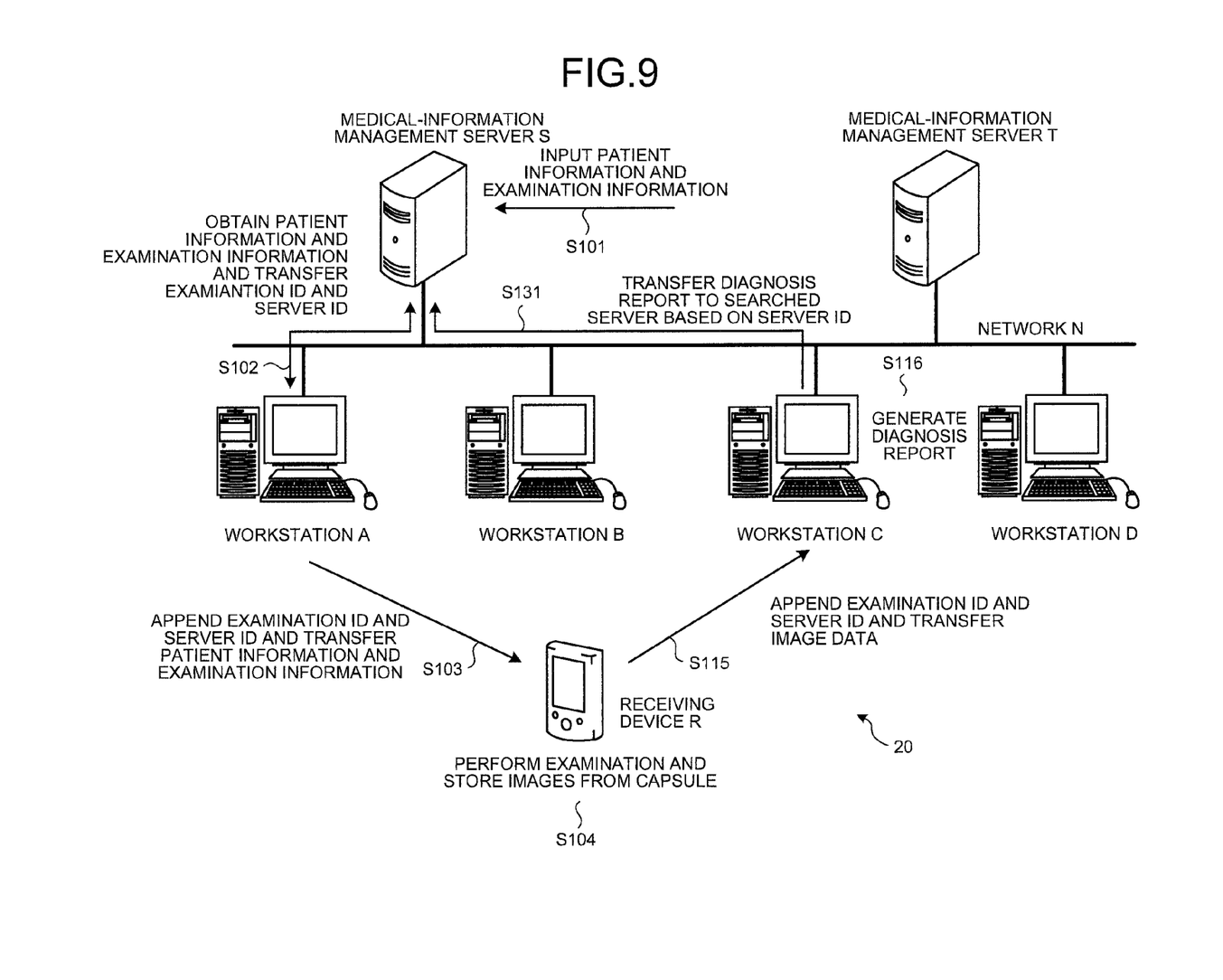
FIG. 9 is a schematic diagram showing an exemplary configuration of a medical-information management network system in accordance with a third embodiment.
Figure 10:
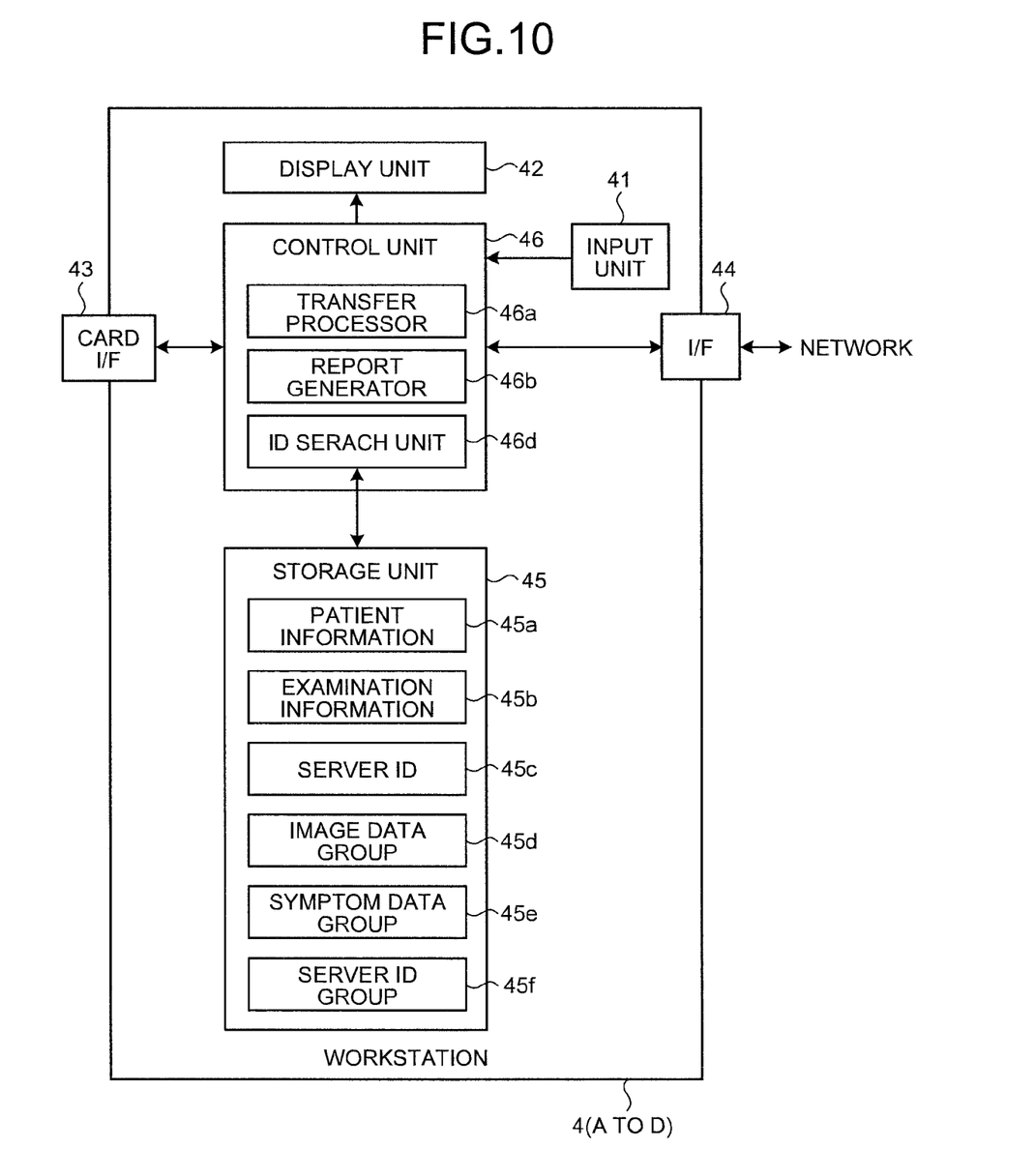
FIG. 10 is a block diagram showing an exemplary configuration of a workstation in the third embodiment.

A medical-information management network system in accordance with a third embodiment is described with reference to FIGS. 9 and 10. The components that are the same as or correspond to those in the first or second embodiments are denoted by the same numerals. FIG. 9 is a schematic diagram showing an exemplary configuration of a medical-information management network system in accordance with the third embodiment. FIG. 10 is a block diagram showing an exemplary configuration of the workstation 4 (A to D) in the third embodiment.

In the third embodiment, the medical-information management network system has a system configuration in which the medical-information management servers S and T are connected to the same network N as shown in FIG. 9. In such a system configuration, the workstation 4 (A to D) includes a storage area 45*f* for storing a server ID group in the storage unit 45 and an ID search unit 46*d* in the control unit 46 instead of the ID determining unit 46*c*.

The storage area 45*f* for storing the server ID group stores the server IDs of the medical-information management servers S and T, which are connected to the network N, and associates the stored server IDs with the medical-information management servers S and T, respectively. When the in-vivo image information is transferred from the receiving device R and then the diagnosis result is to be transferred to the medical-information management server, the ID search unit 46d searches for the medical-information management server that has the same server ID as the server ID that has been transferred from the server ID group stored in the storage area 45f. The ID search unit 46d then controls a process so that the diagnosis result is transferred to the medical-information management server thus searched.

In such a system configuration, an exemplary operation control of a system is described with reference to FIG. 9. This example is similar to that in FIG. 2 and the processes up to Step S104 are the same as those in FIG. 2.

It is assumed that the receiving device R (the information medium 5) is connected to the workstation C after the examination is finished. In this case, similarly to the case in FIG. 8, the transfer processing unit 54a in the receiving device R appends the examination ID and the server ID, which are transferred and stored beforehand, to the in-vivo image information and transfers the in-vivo image information to the workstation C (Step S115). In the workstation C, the report processing unit 46b generates a diagnosis report as a diagnosis result (Step S116). When the diagnosis result is to be transferred to the medical-information management server, the ID search unit 46d in the workstation C searches for the medical-information management server that has the same ID as the server ID that has been transferred and stored from the server ID group stored in the storage area 45f, i.e., searches for the medical-information management server S. Then, the ID search unit 46d controls a process so that the diagnosis result is transferred to the medical-information management server S thus searched (Step S131). The medical-information management server S stores and manages the transferred diagnosis report in association with the examination ID and the like stored therein. The same applies to a case where the receiving device (the information medium 5) is connected to the remaining workstations A, B, D.

Using the server ID as described above, the medical-information management server that has provided the patient information and the examination information can be always identified. The trouble of transferring a diagnosis result to a medical-information management server and storing therein, the server being different from the server that has provided the patient information and examination information, is reliably avoided. Thus, the corresponding diagnosis result is managed at the medical-information management server that has provided the patient information and examination information.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical-information management network system, comprising:
a medical-information management server to which server-identification information is individually given, the medical-information management server configured to manage patient information, examination information, and a diagnosis result;
a receiving device that stores an in-vivo image, which is captured by a body-insertable apparatus inserted into a subject, and information received from the body-insertable apparatus; and
an image display device that is connected with the medical-information management server via a network and obtains the in-vivo image and the information received from the body-insertable apparatus stored in the receiving device, wherein
the image display device comprises a storage unit that stores the server-identification information and the patient information or the examination information which are obtained from the medical-information management server connected via the network, wherein
before the body-insertable apparatus is inserted into the subject, the image display device sets in the receiving device the server-identification information and the patient information or the examination information which are stored in the storage unit, and obtains, when the in-vivo image and the information of the body-insertable apparatus are obtained from the receiving device after the examination, the server-identification information and the patient information or the examination information, wherein
the image display device further comprises:
a determining unit that determines whether the server-identification information received from the receiving device matches the server-identification information stored in the storage unit; and
a control unit that controls the storage unit to store the patient information or the examination information, the in-vivo image and the information of the body-insertable apparatus which are obtained from the receiving device, only when the server-identification information received from the receiving device matches the server-identification information stored in the storage unit.

2. The medical-information management network system according to claim 1, wherein the server-identification information is generated using hardware information of the medical-information management server.

3. The medical-information management network system according to claim 2, wherein the hardware information is a MAC address.

4. The medical-information management network system according to claim 1, wherein the server-identification information is an IP address.

5. The medical-information management network system according to claim 1, wherein the image display device rejects, when the receiving device having the server-identification information that is not stored in the image display device is connected, a reception from the receiving device of the in-vivo image, the information of the body-insertable apparatus, the server-identification information, the patient information, and the examination information.

6. The medical-information management network system according to claim 1, wherein the image display device gives out, when the receiving device having the server-identification information that is not stored in the image display device is connected, a warning to an user.

7. The medical-information management network system according to claim 1, wherein the image display device transfers the diagnosis result to the medical-information management server.

8. The medical-information management network system according to claim 1, wherein the image display device also transfers, when transferring the diagnosis result to the medical-information management server, the server-identification information obtained from the receiving device, and the medical-information management server rejects, when the transferred server-identification information does not match the server-identification information retained in the medical-information management server, a reception of data from the image display device.

9. The medical-information management network system according to claim 1, wherein the image display device also transfers, when transferring the diagnosis result to the medical-information management server, the server-identification information obtained from the receiving device, and the medical-information management server gives out, when the transferred server-identification information does not match the server-identification information retained in the medical-information management server, a warning to the image display device.

10. The medical-information management network system according to claim 7, wherein the medical-information management network system includes a plurality of the medical-information management servers each having different server-identification information, and the image display device searches for the medical-information management server having the same server-identification information as the server-identification information retained in the image display device and transfers the diagnosis result to the medical-information management server thus searched.

11. A medical-information management network system according to claim 1, wherein the information received from the body-insertable apparatus is unit-identification information of the body-insertable apparatus.

12. A medical-information management network system according to claims 1, wherein the diagnosis result is all or a part of images selected from the in-vivo images obtained from the receiving device.

13. A medical-information management network system according to claims 1, wherein the diagnosis result is a report on which a comment of a user is described.

* * * * *